United States Patent [19]

Sauers

[11] 4,225,521

[45] Sep. 30, 1980

[54] HERBICIDAL PHOSPHONATES

[75] Inventor: Richard F. Sauers, Hockessin, Del.

[73] Assignee: E. I. Du Pont de Nemours and Company, Wilmington, Del.

[21] Appl. No.: 930,603

[22] Filed: Aug. 1, 1978

Related U.S. Application Data

[63] Continuation-in-part of Ser. No. 917,388, Jun. 23, 1978, abandoned.

[51] Int. Cl.$^2$ .............................................. C04F 9/02
[52] U.S. Cl. ........................... 260/941; 260/239 BF; 260/326.35; 260/326.42; 260/455 P; 260/465 D; 260/940; 71/86; 71/87; 544/146; 544/157; 546/21; 549/6; 560/20; 560/21; 560/22; 560/23; 560/37; 560/38; 560/55; 560/65; 560/83; 560/100; 560/102; 560/105; 560/125; 560/226
[58] Field of Search .................. 71/86, 106; 260/941

[56] References Cited

U.S. PATENT DOCUMENTS

| | | | |
|---|---|---|---|
| 2,995,486 | 8/1961 | Sallmann | 260/941 |
| 3,093,672 | 6/1963 | Miller | 71/86 |
| 3,170,944 | 2/1965 | Szabo | 71/86 |
| 3,277,147 | 10/1966 | Machleit et al. | 260/941 |
| 3,288,586 | 11/1966 | Littler | 71/113 |
| 3,455,675 | 7/1969 | Irani | 71/86 |
| 3,624,188 | 11/1971 | Curry | 260/941 |
| 3,627,842 | 12/1971 | Nicholson | 260/941 |
| 3,649,722 | 3/1972 | Nicholson | 260/941 |
| 3,772,412 | 11/1973 | Quimby et al. | 260/932 |
| 3,776,984 | 12/1973 | Ratts | 260/941 |
| 3,943,201 | 3/1976 | McIntosh | 71/86 |

FOREIGN PATENT DOCUMENTS 10747 12/1955 Fed. Rep. of Germany ........... 260/941

OTHER PUBLICATIONS

Gutman, "(O-Carbamyl oxime), Phosphate, etc.", (1968), CA71, No. 30236q, (1969).

*Primary Examiner*—Glennon H. Hollrah

[57] ABSTRACT

This invention relates to phosphorus containing compounds which are useful as herbicides.

Additionally, they demonstrate tolerance towards desired crops, e.g., cotton, soybeans and sugarbeets.

8 Claims, No Drawings

HERBICIDAL PHOSPHONATES

Related Application

This application is a continuation-in-part of my copending application U.S. Serial No. 917,388 filed June 23, 1978 now abandoned.

Background of the Invention

German Offenlegungsschrift F107471Vb/120 describes the preparation of compounds of Formula A. These compounds are disclosed to be insecticides.

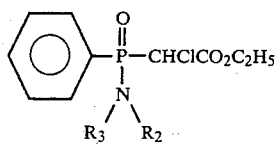

A wherein $R_2$ and $R_3$ are alkyl residues. U.S. Pat. No. 3,627,842 and U.S. Pat. No. 3,772,412 disclose processes for the preparation of compounds of Formula B. These compounds are described as intermediates in the synthesis of detergent builders and lubricant additives.

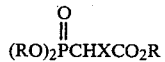

B wherein
X = Cl, Br, I
R = alkyl or aryl residues.

Numerous compounds have been disclosed within recent years which are active herbicides; the need still exists, however, for herbicides which are more active. The presence of undesired vegetation is very damaging to useful crops such as soybeans. In the current world situation, wherein food shortages are acute, it is most important not to lose a significant portion of a valuable crop such as soybeans or peanuts. The presence of undesired vegetation results in the loss of a significant portion of such crops. Thus, the need exists for a particularly effective herbicide which will destroy as much of this unwanted vegetation as is possible without causing significant damage to the desired crops, e.g. soybeans.

According to the instant invention, compounds have been discovered which are highly active herbicides and yet cause minimal damage to certain desired crops, e.g., peanuts, cotton, soybeans and sugarbeets.

Description of the Invention

This invention relates to novel compounds of Formula I, to agricultural compositions containing them and to the method of use of these compounds as pre- and post-emergence herbicides.

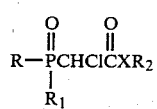

I wherein
X is oxygen or sulphur
R is alkyl of 1–4 carbons, cycloalkyl of 5–8 carbons, alkyl cycloalkyl of 6–8 carbons, cycloalkylalkyl of 6–7 carbons, alkenyl of 3–4 carbons, arylalkyl of 7–8 carbons, thienyl, naphthyl, biphenyl or

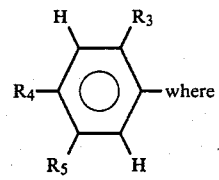 where $R_3$ is H, $C_1$–$C_3$ alkyl, F, Cl, Br, $NO_2$, methoxy,
$R_4$ is H, $C_1$–$C_3$ alkyl, Cl, Br, F, $NO_2$, methoxy, $NR_6R_7$ (where $R_6$ and $R_7$ are independently methyl or ethyl),

$R_9$ and $R_{10}$ are independently H, methyl or ethyl.
$R_5$ is H, $C_1$–$C_3$ alkyl, Cl, Br, F, $NO_2$, $C_1$–$C_3$ alkoxy, $CF_3$, CN,

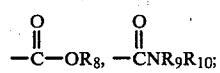

provided that:
(1) Only one of $R_3$, $R_4$, and $R_5$ can be $NO_2$, at the same time,
(2) When $R_4$ is

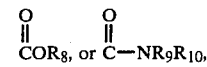

then $R_3$ and $R_5$ are H, Cl, or Br,
(3) When $R_5$ is other than H, Cl, Br or F, then $R_3$ and $R_4$ are H, Cl, Br or F, and
(4) No more than two of $R_3$, $R_4$ or $R_5$ can be alkyl $C_1$–$C_3$, or bromine or alkoxy at the same time,
$R_1$ is phenyl, alkyl or 1–4 carbons, alkenyloxy of 3–4 carbons, alkylthio of 1–3 carbons, alkoxy of 1–4 carbons, $C_2$–$C_3$ alkoxy substituted with alkoxy of 1–3 carbons or with 1–3 chlorines or with one bromine, $NR_{11}R_{12}$, or phenoxy optionally substituted with 1–3 chlorines or 1–3 bromines, 1–2 alkyls of 1–4 carbons, or with $NO_2$;
$R_{11}$ is H, alkyl of 1–4 carbons, cycloalkyl $C_5$–$C_6$ or

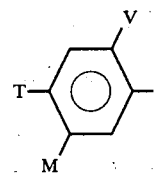

where:
V is H, F, Cl, $NO_2$
T is H, F, Cl, Br, alkyl $C_1$–$C_3$, $CF_3$
M is H, Cl, alkoxy $C_1$–$C_3$, $CF_3$; provided M and T are not simultaneously $CF_3$.
$R_{12}$ is H, methoxy or alkyl of 1–4 carbons; provided that $R_{12}$ is methoxy, $R_{11}$ is hydrogen or methyl;
$R_{11}$ and $R_{12}$ may also be taken together to form a bridge of the structure $-(CH_2)_n-$, $-(CH_2)_2-O-(CH_2)_2-$ or -continued $$-(CH_2)_2-N-(CH_2)_2-$$
$$\phantom{-(CH_2)_2-}|$$
$$\phantom{-(CH_2)_2-}W$$

where n is 4–6 and W is H, methyl or ethyl;

$R_2$ is alkyl of 1–6 carbons or alkenyl of 3–4 carbons, or cycloalkyl of 5–6 carbons optionally substituted with methyl; with the proviso that when $R_2$ is ethyl and R is phenyl, $R_1$ cannot be dialkylamino.

Preferred in order of increasing activity and/or more favorable cost are independently or in combination:

(1) Compounds of Formula I wherein X is oxygen, (2) Compounds of Formula I wherein R is $C_1$–$C_4$ alkyl or phenyl, (3) Compounds of preferred (1) wherein $R_1$ is $C_1$–$C_4$ alkoxy or $NR_{11}R_{12}$ wherein $R_{11}$ and $R_{12}$ are independently H or $C_1$–$C_3$ alkyl or are taken together to form a bridge of the structure $$-(CH_2)_n-, \quad -(CH_2)_2-O-(CH_2)_2- \quad or$$
$$-(CH_2)_2-N-(CH_2)_2-$$
$$\phantom{-(CH_2)_2-}|$$
$$\phantom{-(CH_2)_2-}W$$

where n is 4–6 and W is H, methyl or ethyl, (4) Compounds of preferred (3) wherein R is $C_1$–$C_4$ alkyl or phenyl (5) Compounds of preferred (4) wherein $R_1$ is alkoxy $C_1$–$C_4$;

(6) Compounds wherein $R_2$ is $C_1$–$C_4$ alkyl, especially the compounds of (1), (2), (3), (4), or (5).

Compounds of Formula I specifically preferred for their outstanding activity and/or very favorable cost are:

1-methylethyl 2-chloro-2-[(1-methylethoxy)phenylphosphinyl]acetate 1-methylpropyl 2-chloro-2-[(1-methylethoxy)phenylphosphinyl]acetate 1-methylethyl 2-chloro-2-[(n-butoxy)phenylphosphinyl]acetate 1-methylethyl 2-chloro-2-[(methylethoxy)methylphosphinyl]acetate 1-methylethyl 2-chloro-2-[(ethoxy)methylphosphinyl]acetate 1-methylethyl 2-chloro-2-[(n-propoxy)phenylphosphinyl]acetate 1-methylethyl 2-chloro-2-[(1-methylethoxy)ethylphosphinyl]acetate.

It is to be understood that all isomers of Formula I resulting from asymmetry at the phosphorus and/or carbon atoms are included within the scope of this invention.

Method of Preparation

The compounds of Formula I can be prepared, as is shown in Equation A, by reacting compounds of Formula II with an alkyl or aryl lithium compound at a temperature between −30° and −150° C. followed by contacting the material thus produced with an excess of an aqueous phase of pH below about 6.

Equation A $$\underset{II}{R-\underset{\underset{R_1}{|}}{\overset{\overset{O}{\|}}{P}}-CC l_2C\overset{\overset{O}{\|}}{X}R_2} \quad \xrightarrow[(2)\ H_3O^\oplus]{(1)\ A\ Li} \quad \underset{I}{R-\underset{\underset{R_1}{|}}{\overset{\overset{O}{\|}}{P}}-CHCl\overset{\overset{O}{\|}}{C}XR_2}$$

wherein R-$R_2$ and X are as previously defined, and A is an alkyl or aryl group such as methyl, n-butyl, tert-butyl, or phenyl. Suitable solvents for this reaction include ether, tetrahydrofuran and dioxane. The pH of the aqueous phase may be brought to about 6 or below by the addition of mineral acids such as hydrochloric acid or organic acids such as acetic acid.

Compounds of Formula I can also be prepared from compounds of Formula II using procedures described in U.S. Pat. No. 3,627,842 which is herein incorporated by reference.

Compounds of Formula I can also be prepared, as shown in Equation B, by chlorination of compounds of Formula III with one equivalent of a metal hypochlorite in an aqueous media at a pH greater than seven, and a temperature between 0° C. and 75° C.

Equation B $$\underset{III}{R-\underset{\underset{R_1}{|}}{\overset{\overset{O}{\|}}{P}}-CH_2C\overset{\overset{O}{\|}}{X}R_2} \xrightarrow[H_2O]{1\ eq.M'OCl} \underset{I}{R-\underset{\underset{R_1}{|}}{\overset{\overset{O}{\|}}{P}}-CHCl\overset{\overset{O}{\|}}{C}XR_2}$$

wherein R-$R_2$ and X are as previously defined and M' is Na, K, Li or Ca.

The compounds of Formula II can be prepared, as shown in Equation C, by chlorination of compounds of Formula II with a metal hypochlorite in aqueous media at a pH greater than seven, and a temperature between 0° C. and 75° C. U.S. Pat. No. 3,624,188, herein incorporated by reference, teaches a process for chlorination of phosphonoacetates in a two phase system consisting: (1) of an aqueous phase containing hypochlorite ion; and (2) an inert water-immiscible organic solvent phase in which the chlorinated products formed in the reaction are soluble to the extent of at least five percent by weight. Examples of such solvents are carbon tetrachloride, chloroform and sym-tetrachloroethane.

Equation C $$\underset{III}{\underset{R_1}{\overset{R}{\diagdown}}\!\!\!\overset{\overset{O}{\|}}{\underset{\diagup}{P}}CH_2C\overset{\overset{O}{\|}}{X}R} \xrightarrow[H_2O]{2M'OCl} \underset{II}{\underset{R_1}{\overset{R}{\diagdown}}\!\!\!\overset{\overset{O}{\|}}{\underset{\diagup}{P}}CCl_2C\overset{\overset{O}{\|}}{X}R_2}$$

wherein R-$R_2$, X, and M' are as previously defined.

Compounds of Formula I may also be prepared, as shown in Equation B, by chlorination of compounds of Formula II with sulfuryl chloride or with chlorine in the presence of actinic radiation as described in N. D. Bodnarchuk, V. V. Malovik, and G. I. Derkach J. Gen. Chem. (USSR) 39, 1673–1677 (1968) [CA 71, 12452e (1968)], which is herein incorporated by reference. These reactions may be carried out either without solvent or with the addition of an appropriate inert solvent such as, for example, chloroform, carbon tetrachloride, benzene, or tetrachloroethane.

Equation D

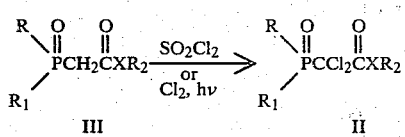

wherein R-R$_2$, and X are as previously defined.

Certain compounds of Formula II can also be prepared by the method described in Equation E.

Equation E

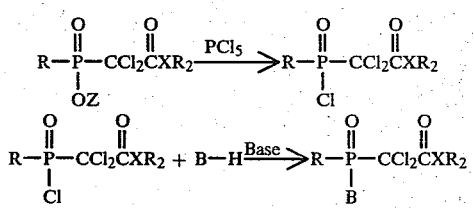

wherein R-R$_2$, and X are as described above and B is an alkoxy, or phenoxy radical or NR$_{11}$R$_{12}$ and Z is C$_1$-C$_4$ alkyl.

The chlorination reaction depicted in Equation E may be carried out at temperatures between about 25° and 100° C. in the absence of an added inert organic solvent.

The second reaction in Equation E may be carried out at temperatures between about −78° and +80° C. in inert organic solvents such as diethylether, tetrahydrofuran, methylene chloride, or carbontetrachloride. Suitable bases include trialkyl amines; N,N-dialkyl anilines, metal alkoxides, and sodium hydride. An excess of trialkylamine may also be used in place of an inert organic solvent.

The compounds of Formula III can be prepared, as shown in Equation F, by reaction of a phosphite of Formula III with an α-haloacetate of Formula V as described in Organophosphorus Compounds — G. M. Kosolapoff, John Wiley and Sons, Inc. New York 1950, pp. 121-123. The reaction may be carried out at temperatures between 50° and 175° C., and either with or without an added inert organic solvent such as benzene, toluene, or xylene.

Equation F

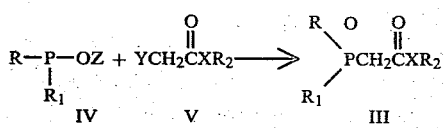

wherein R-R$_2$, and X are as previously defined, Y is chlorine, bromine, or iodine; and Z is an alkyl group of one to six carbons.

Compounds of Formula IV can be prepared by a suitable modification of the methods described in *Organophosphorus Compounds*— G. M. Kosolapoff, John Wiley and Sons Inc., New York, 1950, pp. 180-210, and *Organic Phosphorus Compounds* — Volume 4 — G. M. Kosolapoff and L. Maier, John Wiley and Sons, Inc., 1972, pp. 255-462.

Typical examples of suitable methods for preparing compounds of Formula IV are shown in Equations G, H, and I. The choice of the most suitable method will depend upon the exact nature of the substituents R$_3$-R$_5$, and will be obvious to one skilled in the art.

Equation G

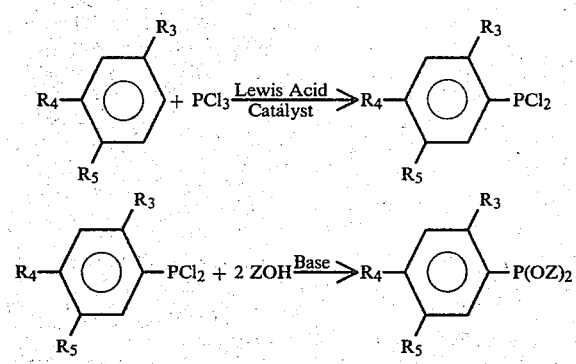

wherein R$_3$-R$_5$, and Z are as defined above.

Equation H

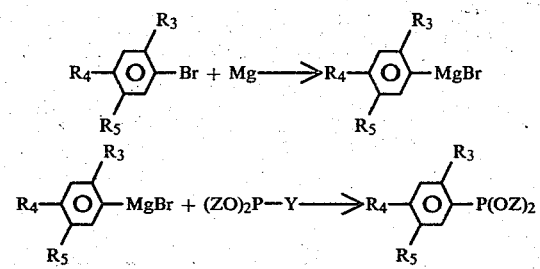

wherein R$_3$-R$_5$, Z and Y are as defined above.

Equation I

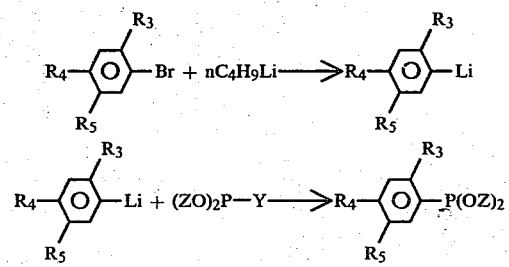

wherein R$_3$-R$_5$, Z, and Y are as defined above.

The following examples specifically illustrate this invention. Unless otherwise indicated, all parts are by weight and all temperatures in °C. Proton NMR data were obtained at 60 MH$_z$ and ambient temperature.

EXAMPLE 1

To a solution of 269 g of phenyl dichloro phosphine in 1.5 liters of tetrahydrofuran at 0-10°, was added a solution of 180 g of 2-propanol and 310 g of triethylamine in 300 ml of tetrahydrofuran. After stirring for 2 hours at room temperature, the mixture was filtered and the filtrate concentrated in vacuo. The residue was distilled to give 209 g of diisopropyl phenylphosphite as a colorless oil bp 62°-63°/0.3 mm Hg.

NMR (CDCl$_3$)δ: 1.2-1.6(m, 12.0 H); 4.2-4.7(m, 1.9 H); 7.6-8.2(m, 5.1 H).

EXAMPLE 2

To 11.8 g of isopropyl bromoacetate was added 15.0 g of diisopropyl phenylphosphite at 80°-110°, while distilling off isopropyl bromide. The reaction mixture was heated to 130° over 30 minutes. Volatile products were removed under 10 mm vacuum at 65°. The yield of 1-methylethyl 2[(1-methylethoxy)phenylphosphinyl]acetate was 18.8 g as a colorless oil.

NMR (CDCl$_3$)δ: 1.1–1.6(m, 12.1 H); 3.2(d, J=17 Hz, 1.7 H); 4.6–5.4(m, 1.8 H); 7.7–8.5(m, 3.5 H).

EXAMPLE 3

A 5.25% commercial grade sodium hypochlorite solution (185 ml—Chlorox®) was cooled to 10° and the pH adjusted to 9.0 with 1N HCl solution. To this solution 15.0 g of 1-methylethyl 2[(1-methylethoxy)phenylphosphinyl]acetate was added at 10°-15° with vigorous stirring. The pH was kept between 9.0 and 9.5 by simultaneous addition of 1N HCl solution (80 ml). The solution was stirred an additional 15 minutes at 15° then extracted with methylene chloride. The methylene chloride solution was dried and stripped to yield 17.0 g of 1-methylethyl 2,2-dichloro-2[(1-methylethoxy)phenylphosphinyl]acetate as a light yellow oil.

NMR (CDCl$_3$)δ: 1.3–1.7(m, 12.3 H); 5.0–5.6(m, 1.8 H); 7.7–8.6(m, 4.9 H).

Anal. Calc'd. for C$_{14}$H$_{19}$Cl$_2$O$_4$P: C, 47.61; H, 5.42; Cl, 20.08. Found: C, 47.21; H, 5.24, 47.05 4.98. Cl, 20.44 20.38.

A sample of this oil slowly crystallized upon standing. It was recrystallized from cyclohexane to give a white solid, m.p. 42°-44°.

EXAMPLE 4

To a solution of 7.1 g of 1-methylethyl 2.2-dichloro-2[(1-methylethoxy)phenylphosphinyl]acetate in 150 ml of ether was added 14 ml of a solution of 1.6 M n-butyl lithium in hexane at -70° over 15 minutes. The solution was then allowed to warm to -10° before adding 60 ml of 0.5 M aqueous HCl solution at -10° to 0°. The phases were separated and the organic phase washed with water then 5% NaHCO$_3$ solution. The solution was then dried and stripped to give 5.0 g of 1-methylethyl 2-chloro-2[(1-methylethoxy)phenylphosphinyl]acetate as a light yellow oil N$_D^{25}$ 1.5057.

NMR (CDCl$_3$)δ1.2–1.7(m, 12.5 H); 4.6–5.5(m, 2.7 H, J$_{PCH}$=14 Hz); 7.4–8.5(m, 4.9 H).

Mass Spectrum shows M+1 ion at 319, and sequential loss of two molecules of propylene to give peaks at 276 and 234.

Using suitable modifications of the procedure described in the above examples, the compounds of Formula I described in Table I can be prepared.

TABLE 1

$$\begin{array}{c} R \diagdown \overset{O}{\underset{}{\|}} \quad \overset{O}{\underset{}{\|}} \\ P-CClCXR_2 \\ R_1 \diagup \quad | \\ \phantom{R_1 \diagup} \quad H \end{array}$$

| R | R$_1$ | X | R$_2$ | N$_D$(°C.) | m.p |
|---|---|---|---|---|---|
|  | CH$_3$O— | O | CH$_3$\|nC$_4$H$_9$CH— | | |
|  | (CH$_3$)$_2$CHO— | O | (CH$_3$CH$_2$)$_2$CH— | | |
|  | (CH$_3$)$_2$CHO— | O | C$_2$H$_5$— | | |
|  | (CH$_3$)$_2$CHO— | O | CH$_3$\|C$_2$H$_5$CH— | 1.5002(25°) | |
|  | CH$_2$=C—CH$_2$O—\|CH$_3$ | O | (CH$_3$)$_2$CH— | | |
|  | n-C$_6$H$_{13}$O— | O | C$_2$H$_5$— | | |
|  | (CH$_3$)$_2$CHO— | O | CH$_3$\|(CH$_3$)$_2$CHCH— | | |
|  | (CH$_3$)$_2$CHO— | O | CH$_2$=CH—CH—\|CH$_3$ | | |

TABLE 1-continued $$\underset{R_1}{\overset{R}{\vphantom{|}}}\underset{\underset{H}{|}}{\overset{\overset{O}{\|}}{P}}-\underset{}{\overset{\overset{O}{\|}}{C}}ClCXR_2$$

| R | $R_1$ | X | $R_2$ | $N_D(°C.)$ | m.p |
|---|---|---|---|---|---|
|  | $(CH_3)_2CHO-$ | S | $(CH_3)_2CH-$ | | |
|  | $(CH_3)_2CHO-$ | S | $C_2H_5\underset{\underset{CH_3}{\|}}{CH}-$ | | |
|  | $CH=CH-CH_2O-$ | O | $(CH_3)_2CH-$ | | |
|  | $NH_2-$ | O | $(CH_3)_2CH-$ | | |
|  | $CH_3CH_2O-$ | O | $CH_2=CHCH_2-$ | | |
|  | $(CH_3)_2CHO-$ | O | $CH_2=\underset{\underset{CH_3}{\|}}{C}-CH_2-$ | | |
|  | $nC_4H_9O-$ | O | $(CH_3)_2CH-$ | | |
|  | $n\text{-}C_3H_7O-$ | O | $(CH_3)_2CH-$ | | |
|  | $(CH_3)_2CHO-$ | O | $CH_3-$ | | |
|  | $CH_3O-$ | O | $(CH_3)_2CH-$ | | |
|  | $CH_3CH_2O-$ | O | $(CH_3)_2CH-$ | | |
|  | $CH_3CH_2O-$ | O | $CH_3CH_2-$ | | |
|  | $(CH_3)_2CHO-$ | O | $nC_3H_7\underset{\underset{CH_3}{\|}}{CH}-$ | | |
|  | $CH_3S-$ | O | $(CH_3)_2CH-$ | | |
|  | $(CH_3)_2CHS-$ | O | $(CH_3)_2CH-$ | | |

TABLE 1-continued $$\begin{array}{c} R \\ \diagdown \\ R_1 \end{array} \overset{O}{\underset{\parallel}{P}} - \overset{O}{\underset{H}{\overset{\parallel}{C}}} - CClCXR_2$$

| R | $R_1$ | X | $R_2$ | $N_D(°C.)$ | m.p |
|---|---|---|---|---|---|
| 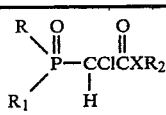 | $(CH_3)_2CHS-$ | S | $(CH_3)_2CH-$ | | |
|  |  | O | $(CH_3)_2CH-$ | | 181°–182° |
|  | $CH_3-$ | O | $C_2H_5CH-$<br>$\;\;\;\;\;\;\;\;\vert$<br>$\;\;\;\;\;\;\;\;CH_3$ | | |
| 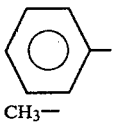 | $C_2H_5-$ | O | $C_2H_5CH-$<br>$\;\;\;\;\;\;\;\;\vert$<br>$\;\;\;\;\;\;\;\;CH_3$ | | |
|  | $\;\;\;\;\;\;\;\;CH_3$<br>$\;\;\;\;\;\;\;\;\vert$<br>$CH_3CH_2CH-$ | O | $(CH_3)_2CH-$ | | |
|  | $CH_3O(CH_2)_3O-$ | O | $(CH_3)_2CH-$ | | |
|  | $ClCH_2CH_2O-$ | O | $(CH_3)_2CH-$ | | |
| 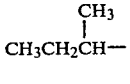 | $BrCH_2CH_2CH_2O-$ | O | $\;\;\;\;\;\;\;\;CH_3$<br>$\;\;\;\;\;\;\;\;\vert$<br>$CH_3CH_2CH-$ | | |
|  | $Cl_3CCH_2O-$ | O | $C_2H_5CH-$<br>$\;\;\;\;\;\;\;\;\vert$<br>$\;\;\;\;\;\;\;\;CH_3$ | | |
|  |  | O | $(CH_3)_2CH-$ | | |
|  |  | O | $(CH_3)_2CH-$ | | |
| 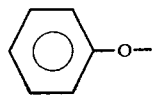 |  | O | $(CH_3)_2CH-$ | | |
|  |  | O | $(CH_3)_2CH-$ | | |
| 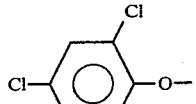 |  | S | $(CH_3)_2CH-$ | | |

TABLE 1-continued $$\underset{R_1}{\overset{R}{\underset{|}{P}}}\overset{O}{\underset{||}{-}}\underset{H}{\overset{|}{C}Cl}\overset{O}{\underset{||}{C}}XR_2$$

| R | R₁ | X | R₂ | $N_D$(°C.) | m.p |
|---|---|---|---|---|---|
|  | 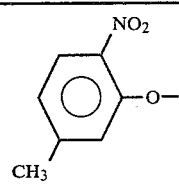 | O | $(CH_3)_2CH-$ | | |
|  | 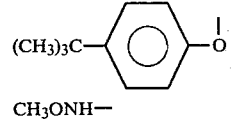 | O | $(CH_3)_2CH-$ | | |
|  | $CH_3ONH-$ | O | $\underset{CH_3}{\overset{|}{C_2H_5CH-}}$ | | |
|  | $\underset{CH_3}{\overset{|}{CH_3O-N-}}$ | O | $\underset{CH_3}{\overset{|}{C_2H_5CH-}}$ | | |
|  | $(CH_3)_2N-$ | O | $(CH_3)_2CH-$ | | |
|  | $(nC_4H_9)_2N-$ | O | $(CH_3)_2CH-$ | | |
|  | $(CH_3)_2CH-NH-$ | O | $\underset{CH_3}{\overset{|}{C_2H_5CH-}}$ | | |
|  | 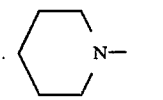 | O | $(CH_3)_2CH-$ | | |
|  | 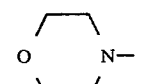 | O | $(CH_3)_2CH-$ | | |
|  | 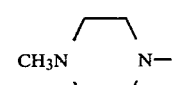 | O | $(CH_3)_2CH-$ | | |
|  | $[(CH_3)_2CH]_2N-$ | O | $(CH_3)_2CH-$ | | |
|  | $(C_2H_5)_2N-$ | O | $\underset{CH_3}{\overset{|}{C_2H_5CH-}}$ | | |
|  | 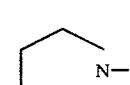 | O | $(CH_3)_2CH-$ | | |
|  | 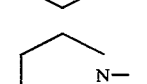 | O | $(CH_3)_2CH-$ | | |

TABLE 1-continued
$$\underset{R_1}{\overset{R}{\underset{\|}{P}}}\underset{H}{\overset{O}{\underset{\|}{C}Cl\overset{O}{\underset{\|}{C}}XR_2}}$$
| R | R₁ | X | R₂ | $N_D(°C.)$ | m.p |
|---|---|---|---|---|---|
|  | (CH₃)₃CNH— | O | (CH₃)₂CH— | | |
|  | (CH₃)₂N— | S | (CH₃)₂CH— | | |
|  | (CH₃)₂N— | O | CH₂=CH—CH—<br>           \|<br>           CH₃ | | |
|  | 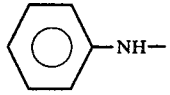—NH— | O | (CH₃)₂CH— | | |
|  | 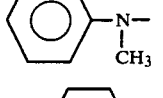—N—<br>         \|<br>         CH₃ | O | (CH₃)₂CH— | | |
|  | 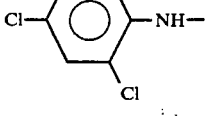—NH— | O | (CH₃)₂CH— | | |
|  | 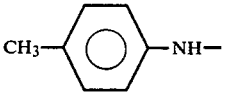—NH— | O | (CH₃)₂CH— | | |
|  | 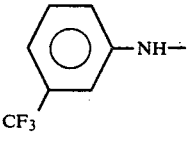—NH— | O | (CH₃)₂CH— | | |
|  | 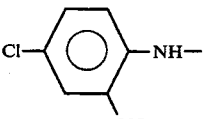—NH— | O | (CH₃)₂CH— | | |
|  | 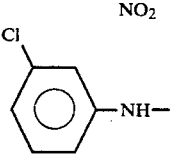—NH— | O | (CH₃)₂CH— | | |
|  | —NH— | O | (CH₃)₂CH— | | |
|  | 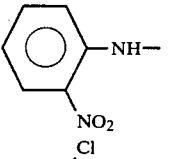—NH— | O | (CH₃)₂CH— | | |
|  | 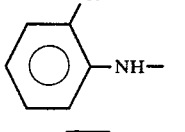—NH— | O | (CH₃)₂CH— | | |
|  | Cl—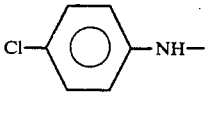—NH— | O | (CH₃)₂CH— | | |

TABLE 1-continued $$\begin{array}{c} R \quad O \quad\quad O \\ \diagdown \parallel \quad\quad \parallel \\ P-CClCXR_2 \\ \diagup \quad | \\ R_1 \quad H \end{array}$$

| R | R₁ | X | R₂ | $N_D$(°C.) | m.p |
|---|---|---|---|---|---|
| 4-Cl-C₆H₄— | CH₃CH₂O— | O | CH₃CH₂— | | |
| 4-Cl-C₆H₄— | CH₃CH₂O— | O | (CH₃)₂CH— | | |
| 4-Cl-C₆H₄— | (CH₃)₂CHO— | O | (CH₃)₂CH— | | |
| 4-Cl-C₆H₄— | (CH₃)₂CHO— | O | C₂H₅CH(CH₃)— | | |
| 4-Br-C₆H₄— | CH₃CH₂O— | O | (CH₃)₂CH— | | |
| 3,4-Cl₂-C₆H₃— | CH₃CH₂O— | O | (CH₃)₂CH— | | |
| 2-Cl-4-Me₂N-C₆H₃— | CH₃CH₂O— | O | (CH₃)₂CH— | | |
| 2,5-(CH₃)₂-C₆H₃— | (CH₃)₂CHO— | O | (CH₃)₂CH— | 1.5078(25°) | |
| 3,5-(CH₃)₂-C₆H₃— | (CH₃)₂CHO— | O | (CH₃)₂CH— | | |
| 4-(CH₃)₂CH-C₆H₄— | (CH₃)₂CHO— | O | (CH₃)₂CH— | | |
| 2-C₂H₅-C₆H₄— | CH₃CH₂O— | O | (CH₃)₂CH— | 1.5088(25°) | |
| 2-NO₂-C₆H₄— | (CH₃)₂CHO— | O | (CH₃)₂CH— | | |

TABLE 1-continued $$\overset{R}{\underset{R_1}{\overset{O}{\underset{\|}{P}}}}-\overset{O}{\underset{H}{\overset{\|}{C}Cl}}CXR_2$$

| R | $R_1$ | X | $R_2$ | $N_D$(°C.) | m.p |
|---|---|---|---|---|---|
| 2-NO$_2$-phenyl | (CH$_3$)$_2$CHO— | O | (CH$_3$)$_2$CH— | | |
| 4-O$_2$N-phenyl | (CH$_3$)$_2$CHO— | O | (CH$_3$)$_2$CH— | | |
| 3-NO$_2$-4-CH$_3$-phenyl | (CH$_3$)$_2$CHO— | O | (CH$_3$)$_2$CH— | | |
| 2-F-phenyl | CH$_3$CH$_2$O— | O | (CH$_3$)$_2$CH— | | |
| 3-F-phenyl | CH$_3$CH$_2$O— | O | (CH$_3$)$_2$CH— | | |
| 4-F-phenyl | CH$_3$CH$_2$O— | O | (CH$_3$)$_2$CH— | | |
| 4-F-phenyl | CH$_3$CH$_2$O— | O | CH$_3$CH$_2$CH(CH$_3$)— | 1.4942(25°) | |
| 4-Me$_2$N-phenyl | CH$_3$CH$_2$O— | O | (CH$_3$)$_2$CH— | | |
| 3-Cl-phenyl | CH$_3$CH$_2$O— | O | (CH$_3$)$_2$CH— | | |
| 2,4-Cl$_2$-phenyl | CH$_3$CH$_2$O— | O | (CH$_3$)$_2$CH— | | |
| 2-Br-phenyl | CH$_3$CH$_2$O— | O | (CH$_3$)$_2$CH— | | |
| 4-(C$_2$H$_5$OC(O))-phenyl | (CH$_3$)$_2$CHO— | O | (CH$_3$)$_2$CH— | | |

TABLE 1-continued $$\underset{R_1}{\overset{R}{\diagdown}}\underset{\parallel}{\overset{O}{P}}-\underset{H}{\overset{\parallel}{C}Cl}\overset{O}{\overset{\parallel}{C}}XR_2$$

| R | R₁ | X | R₂ | $N_D$(°C.) | m.p |
|---|---|---|---|---|---|
| 4-(CH₃)₂NC(O)-C₆H₄- | (CH₃)₂CHO— | O | (CH₃)₂CH— | | |
| 4-[CH₃N(C₆H₅)C(O)]-C₆H₄- | (CH₃)₂CHO— | O | (CH₃)₂CH— | | |
| 4-O₂N-C₆H₄- | (CH₃)₂N— | O | (CH₃)₂CH— | | |
| 4-O₂N-C₆H₄- | C₆H₅O— | O | (CH₃)₂CH— | | |
| 2,4-Cl₂-C₆H₃- | (CH₃)₂N— | O | (CH₃)₂CH— | | |
| 2,4-Cl₂-C₆H₃- | C₆H₅O— | O | (CH₃)₂CH— | | |
| 2,4-(CH₃)₂-C₆H₃- | 2-NO₂-4-CH₃-C₆H₃O— | O | (CH₃)₂CH— | | |
| 3-Cl-C₆H₄- | (CH₃)₂CHS— | O | (CH₃)₂CH— | | |
| 3-F-C₆H₄- | (CH₃)₂N— | S | (CH₃)₂CH— | | |
| 4-C₂H₅OC(O)-C₆H₄- | (CH₃)₂N— | O | (CH₃)₂CH— | | |
| 4-(CH₃)₂NC(O)-C₆H₄- | (CH₃)₂N— | O | (CH₃)₂CH— | | |
| CH₃— | (CH₃)₂CHO— | O | (CH₃)₂CH— | 1.4541(25°) | |

TABLE 1-continued $$\begin{array}{c} R \quad O \quad\quad O \\ \diagdown \parallel \quad\quad \parallel \\ P-CClCXR_2 \\ \diagup \quad\quad | \\ R_1 \quad\quad H \end{array}$$

| R | $R_1$ | X | $R_2$ | $N_D$(°C.) | m.p |
|---|---|---|---|---|---|
| $CH_3-$ | $CH_3CH_2O-$ | O | $(CH_3)_2CH$ | | |
| $C_2H_5-$ | $CH_3CH_2O-$ | O | $(CH_3)_2CH$ | | |
| $C_2H_5-$ | $(CH_3)_2CHO-$ | O | $(CH_3)_2CH-$ | 1.4524(25°) | |
| $(CH_3)_3C-$ | $CH_3O-$ | O | $C_2H_5-CH-$<br>$\quad\quad\quad\vert$<br>$\quad\quad\quad CH_3$ | | |
| $C_2H_5-$ | $C_2H_5-$ | O | $C_2H_5-CH-$<br>$\quad\quad\quad\vert$<br>$\quad\quad\quad CH_3$ | | |
| $C_2H_5-$ | $n-C_4H_9O-$ | O | $C_2H_5-CH-$<br>$\quad\quad\quad\vert$<br>$\quad\quad\quad CH_3$ | | |
| 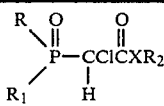 | $C_2H_5O-$ | O | $C_2H_5-CH-$<br>$\quad\quad\quad\vert$<br>$\quad\quad\quad CH_3$ | 1.5080 | |
| $CH_3-$ | $(CH_3)_2N-$ | O | $(CH_3)_2CH-$ | | |
|  | $(CH_3)_2N-$ | O | $(CH_3)_2CH-$ | | |
|  | $CH_3-$ | O | $(CH_3)_2CH$ | | |
| 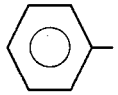 | $(CH_3)_2CHO-$ | O | $(CH_3)_2CH-$ | | |
|  | $(CH_3)_2CHO-$ | O | $(CH_3)_2CH-$ | | |
| 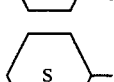 | $(CH_3)_2CHO-$ | O | $(CH_3)_2CH-$ | | |
| 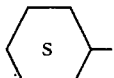 | $(CH_3)_2N-$ | O | $(CH_3)_2CH-$ | | |
| 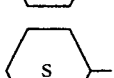 | $(CH_3)_2CHO-$ | O | $(CH_3)_2CH-$ | | |
|  | $(CH_3)_2CHO-$ | O | $(CH_3)_2CH-$ | | |
| 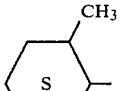 | $(CH_3)_2CHO-$ | O | $(CH_3)_2CH-$ | | |
| 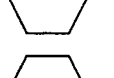 | $(CH_3)_2N-$ | O | $(CH_3)_2CH-$ | | |
| $(CH_3)_3C-$ | $(CH_3)_2N-$ | O | $(CH_3)_2CH-$ | | |
| $CH_3-$ | $CH_3-$ | O | $(CH_3)_2CH-$ | | |
| 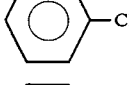 | $(CH_3)_2CH-$ | O | $(CH_3)_2CH-$ | | |

TABLE 1-continued $$\underset{R_1}{\overset{R}{\underset{\|}{P}}}\underset{H}{\overset{O}{\|}}\underset{}{CClC}\overset{O}{\underset{\|}{X}}R_2$$

| R | R₁ | X | R₂ | $N_D$(°C.) | m.p |
|---|---|---|---|---|---|
| 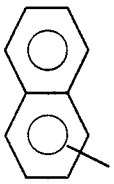 | (CH₃)₂N— | O | (CH₃)₂CH— | | |
| (CH₃)₃C— 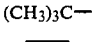 | (CH₃)₂CHO—<br>(CH₃)₂CHO— | O<br>O | (CH₃)₂CH—<br>n-C₃H₇CHCH—<br>$\|$<br>CH₃ | | |
| 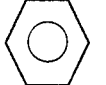 | (CH₃)₂CHO— | O | (C₂H₅)₂CH— | | |
|  | (CH₃)₂CHO— | O | (CH₃)₂CHCH—<br>$\|$<br>CH₃ | | |
| 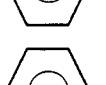 | (CH₃)₂CHOCH₂CH₂CH₂ | O | (CH₃)₂CH— | | |
|  | (CH₃)₂CHOCH₂CH₂O— | O | (CH₃)₂CH— | | |
|  | C₂H₅OCH₂CH₂CH₂O— | O | (CH₃)₂CH— | | |
|  | C₂H₅OCH₂CH₂O— | O | (CH₃)₂CH— | | |
| 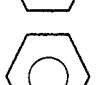 | CH₃OCH₂CH₂O— | O | (CH₃)₂CH— | | |
| 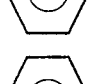 |  | O | (CH₃)₂CH— | | |
| 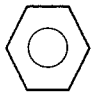 |  | O | (CH₃)₂CH— | | |
| 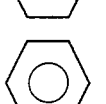 |  | O | (CH₃)₂CH— | | |
| 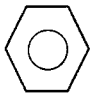 |  | O | (CH₃)₂CH— | | |

TABLE 1-continued
$$\underset{R_1}{\overset{R}{\diagdown}}\underset{H}{\overset{O}{\overset{\|}{P}}}-\underset{H}{\overset{}{\underset{|}{C}Cl}}\overset{O}{\overset{\|}{C}}XR_2$$
| R | R₁ | X | R₂ |
|---|---|---|---|
|  | 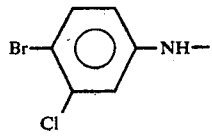 (Br, Cl, NH—) | O | (CH₃)₂CH— |
|  | 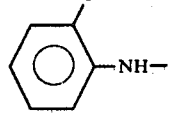 (F, NH—) | O | (CH₃)₂CH— |
|  | 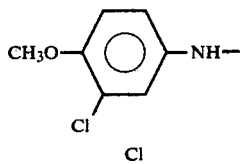 (CH₃O, Cl, NH—) | O | (CH₃)₂CH— |
|  | 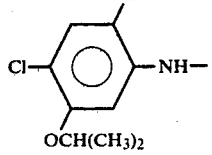 (Cl, Cl, OCH(CH₃)₂, NH—) | O | (CH₃)₂CH— |
|  | 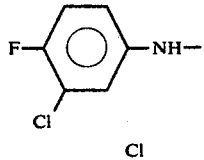 (F, Cl, NH—) | O | (CH₃)₂CH— |
|  | 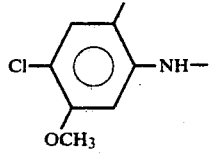 (Cl, Cl, OCH₃, NH—) | O | (CH₃)₂CH— |
|  | 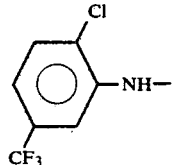 (Cl, CF₃, NH—) | O | (CH₃)₂CH— |
|  | 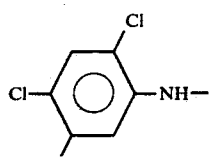 (Cl, Cl, Cl, NH—) | O | (CH₃)₂CH— |
|  | 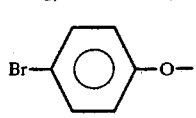 (Br, O—) | O | (CH₃)₂CH— |
|  | 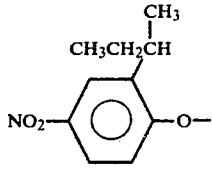 (CH₃CH₂CH(CH₃), NO₂, O—) | O | (CH₃)₂CH— |

TABLE 1-continued $$\underset{R_1}{\overset{R}{\underset{|}{P}}}\overset{\overset{O}{\|}}{-}\underset{H}{\overset{O}{\underset{|}{C}Cl}}\overset{O}{\overset{\|}{C}}XR_2$$

| R | R₁ | X | R₂ | N_D(°C.) | m.p |
|---|---|---|---|---|---|
|  CH(CH₃)₂ | (CH₃)₂CHO— | O | —CH₂CH=CH₂ | | |
|  CH(CH₃)₂ (with second CH(CH₃)₂) | (CH₃)₂CHO— | O | (CH₃)₂CH— | | |
|  CH₃ | (CH₃)₂CHO | O | (CH₃)₂CH— | | |
|  Br | (CH₃)₂CHO | O | (CH₃)₂CH— | | |
|  NO₂ | (CH₃)₂CHO | O | (CH₃)₂CH— | | |
|  CN | (CH₃)₂CHO | O | (CH₃)₂CH— | | |
|  CO₂CH₃ | (CH₃)₂CHO | O | (CH₃)₂CH— | | |
|  CO₂C(CH₃)₃ | (CH₃)₂CHO | O | (CH₃)₂CH— | | |
|  CON(CH₃)₂ | (CH₃)₂CHO— | O | (CH₃)₂CH— | | |
|  | CH₃CH₂CHO— (with CH₃ branch) | O | (CH₃)₂CH— | | |
|  | (CH₃)₂CHCH₂O— | O | (CH₃)₂CH— | | |
|  | CH₃CH₂CHO— (with CH₃ branch) | O | CH₃CH₂CH— (with CH₃ branch) | | |

TABLE 1-continued $$\begin{array}{c} R \quad O \quad\quad O \\ \phantom{R_1}\diagdown\|\phantom{xx}\| \\ \phantom{xxx}P-CClCXR_2 \\ \diagup\phantom{xxxx}| \\ R_1\phantom{xxx}H \end{array}$$

| R | $R_1$ | X | $R_2$ | $N_D$(°C.) | m.p |
|---|---|---|---|---|---|
| 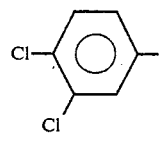 | $(CH_3)_2CHO-$ | O | $(CH_3)_2CH-$ | | |
| 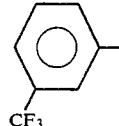 | $(CH_3)_2CHO-$ | O | $(CH_3)_2CH-$ | | |
| 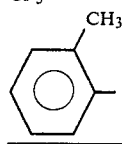 | $(CH_3)_2CHO-$ | O | $(CH_3)_2CH-$ | | |

Useful formulations of the compounds of Formula I can be prepared in conventional ways. They include dusts, granules, pellets, solutions, emulsions, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions.

| | Percent by Weight | | |
|---|---|---|---|
| | Active Ingredient(s) | Diluent(s) | Surfactant(s) |
| Emulsions, Solutions (including Emulsifiable Concentrates) | 5–50 | 40–95 | 0–15 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.Y. The denser diluents are preferred to dust. Typical liquid diluents and solvents are described in Marsden, "Solvents Guide", 2nd Edn., Interscience, New York 1950. Solution concentrates are preferably stable against phase separation at 0° C. "McCutcheon's Detergents and Emulsifiers Annual", Allured Publ. Corp., Ridgwood, N.J., as well as Sisely and Wood, "Encyclopedia of Surface Active Agents", Chemical Publ. Co., Inc. New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5 Line 43, through Col. 7, line 62 and Ex. 8, 12, 15, 39, 41, 52, 53, 58, 132, 138–140, 162–164, 166, 167, and 169–182.

H. Gysin and E. Knusli, U.S. Pat. No. 2,891,855, June 23, 1959, Col. 3 Line 66 through Col. 5, Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 8

Emulsifiable Concentrate

| | |
|---|---|
| 1-methylethyl 2-chloro-2-[(1-methylethoxy)methylphosphinyl]-acetate | 25% |
| blend of oil soluble sulfonates and polyoxyethylene ethers | 6% |
| cumene range aromatic solvent | 69% |

The ingredients are combined and stirred with gentle warming to speed solution. A fine screen filter is included in packaging operation to insure the absence of any extractions undissolved material in the product.

EXAMPLE 9

Pellets - Granules

| | |
|---|---|
| 1-methylethyl 2-chloro-2-[(1-methylethoxy)phenylphosphinyl]acetate | 15% |
| anhydrous sodium sulfate | 10% |
| crude calcium ligninsulfonate | 5% |
| sodium alkylnaphthalenesulfonate | 1% |
| calcium/magnesium bentonite | 69% |

The ingredients are blended and moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 10

Solution Concentrate

| | |
|---|---|
| 1-methylethyl 2-chloro-2-[(1-methylethoxy)phosphinyl]acetate | 36% |
| blend of oil soluble sulfonates and polyoxyethylene ethers | 8% |
| 2-butoxyethanol | 56% |

The ingredients are combined and stirred until solution is effected. After filtration, the liquid may be used directly in LV or ULV applications or may be diluted with solvent or water before spraying.

EXAMPLE 11

Granules

| | |
|---|---|
| 1-methylpropoxy 2-chloro-2-[(1-methylethyl)phenylphosphinyl]acetate; | 5% |
| preformed bentonite granules, 20–50 mesh | 95% |

The active ingredient is dissolved in isopropanol to make a 20% solution which is then sprayed on the preformed granules as they are tumbled in a double cone blender. After drying to remove solvent, the granules are packaged.

Utility

The compounds of the present invention are useful for the control of undesired vegetation. They can be used for the selective control of weeds in crops, such as cotton, soybeans and sugarbeets, or wherever general weed control is required, such as on industrial sites, railroad rights-of-way and locations adjacent to croplands.

The precise amount of the compounds of the present invention to be used in any given situation will vary according to the particular end result desired, the use involved, the plant and soil involved, the formulations used, the mode of application, prevailing weather conditions, foliage density and like factors. Since so many variables play a role, it is not possible to state a rate of application suitable for all situations. Broadly speaking, the compounds of the invention are used at levels of about 0.06 to about 15 kilograms per hectare. The lower rates in this range will generally be selected for selective weed control in crops, on lighter soils, soils low in organic matter content, or in situations where maximum persistence is not necessary. In many situations, it is advantageous to incorporate these chemicals with the soil.

The compounds of the present invention may be combined with any other herbicide and they are particularly useful in combination with herbicides of the substituted urea, uracil or s-triazine types for controlling a broad spectrum of weeds.

The following herbicidal compounds may be used in combination with the compounds of the instant invention:

5-amino-4-chloro-2-phenyl-3(2 H)-pyridazinone (Pyrazon)

2-chloro-4,6-bis(ethylamino)-s-triazine (Simazine)

2-chloro-4-(ethylamino)-6-(isopropylamino)-s-triazine (Atrazine)

2-chloro-4,6-bis(isopropylamino)-s-triazine (Propazine)

2-[[4-chloro-6-(ethylamino)-s-triazin-2-yl]amino]-2-methylproprionitrile (Cyanazine)

4-amino-6-(1,1-dimethylethyl)-3-(methylthio)-1,2,4-triazin-5(4 H)-one (Metribuzin)

3-(3,4-dichlorophenyl)-1,1-dimethylurea (Diuron)

3-(p-chlorophenoxy)phenyl]-1,1-dimethylurea (Chloroxuron)

1,1-dimethyl-3-(α,α,α-trifluoro-m-tolyl)urea (Fluorometuron)

3-(3,4-dichlorophenyl)-1-methoxy-1-methylurea (Linuron)

5-bromo-3-sec-butyl-6-methyluracil (Bromacil)

3-cyclohexyl-5,6-trimethyleneuracil (Lenacil)

2-chloro-1(3-ethoxy-4-nitrophenoxy)-4-trifluoromethylbenzene 3-isopropyl-(1 H)-2,1,3-benzothiadiazin-4(3 H)-one, 2,2-dioxide (Bentazone)

1,1'-dimethyl-4,4'-bipyridium ion (Paraquat)

2,4-dichlorophenoxy acetic acid and salts

5-[2-chloro-4-(trifluoromethyl)phenoxy]-2-nitrobenzoic acid, sodium salts (Blazer ®)

Herbicidal activity of the subject compounds was discovered in a number of greenhouse tests, as described below.

Test A

Seeds of crabgrass (Digitaria spp.), barnyardgrass (Echinochloa crusgalli), wild oats (Avena fatua), cassia (Cassia tora), morningglory (Impomea spp.), cocklebur (Xanthium spp.), sorghum, corn, soybeam, rice, wheat as well as nutsledge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

B=burn; G=growth retardation; C=chlorosis/necrosis; D=defoilation; E=emergence inhibition; X=axillary stimulation; and H=formative effects. The ratings for the compounds tested by this procedure are presented in Table A. It will be seen that certain of the compounds tested have utility for selective pre-emergence weed control in soybeans.

TABLE A

| kg/ha | Ph-P(O)(OiPr)-CHCl-C(O)-O-iPr | | (Ph)$_2$-P(O)-CHCl-C(O)-O-iPr | | Ph-P(O)(OiPr)-CHCl-C(O)-O-iPr (variant) | | CH$_3$-P(O)(OiPr)-CHCl-C(O)-O-iPr |
|---|---|---|---|---|---|---|---|
| | 2 | 0.4 | 2 | 0.4 | 2 | 0.4 | 0.4 |
| POST EMERGENCE | | | | | | | |
| BUSH BEAN | 1B,7H | — | 0 | 0 | 2B,3H | 1C,1H | 1H |
| COTTON | 2B,5D,8G | 1B,4G | 0 | 0 | 4B | 2B | 1B,1H |
| MORNING GLORY | 1B,8H | 1B,4G | 0 | 0 | 1B,5H | 1B | 0 |
| COCKLEBUR | 1B | 0 | 0 | 0 | 1H | 0 | 0 |
| CASSIA | 1B,6H | 5H | 0 | 0 | 7H | 0 | 0 |
| NUTSEDGE | 8G | 8G | 0 | 0 | 8G | 1C,5G | 0 |
| CRABGRASS | 8H | 9H | 5G | 0 | 9H | 8H | 5H |
| BARNYARD GRASS | 2B,9H | 9H | 4G | 0 | 3C,9H | 8H | 2H |
| WILD OATS | 2B,8H | 8H | 0 | 0 | 9H | 0 | 0 |
| WHEAT | 2B,8G | 8G | 0 | 0 | 9G | 2G | 0 |
| CORN | 9H | 8H | 0 | 0 | 9H | 6G | 0 |
| SOYBEAN | 1B,7H | 5H | 0 | 0 | 6H | 1H | 3H |
| RICE | 1B,8G | 8G | 0 | 0 | 1B,9G | 5G | 3G |
| SORGHUM | 1B,9H | 9H | 0 | 0 | 1B,9H | 0 | 0 |
| PRE EMERGENCE | | | | | | | |
| MORNING GLORY | 10C | 2C,7G | 0 | 0 | 10C | 2H | 4H |
| COCKLEBUR | 2G | 0 | 0 | 0 | 1H | 0 | 2H |
| CASSIA | 10C | 2C,8G | 0 | 0 | 2C,8G | 1H | 5H |
| NUTSEDGE | 10E | 10E | 6G | 6G | 10E | 10E | 9G |
| CRABGRASS | 10E | 9H | 10H | 9H | 10E | 10H | 9H |
| BARNYARD GRASS | 10H | 10H | 9H | 9H | 10H | 10H | 9H |
| WILD OATS | 10H | 9H | 8H | 5G | 9H | 8H | 8H |
| WHEAT | 10H | 9H | 9G | 9G | 9H | 9H | 9H |
| CORN | 9H | 9H | 9H | 8H | 10H | 9H | 9H |
| SOYBEAN | 9H | 9H | 1H | 0 | 6H | 5G | 5H |
| RICE | 10E | 10E | 9G | 9G | 10E | 9G | 9H |
| SORGHUM | 9H | 10H | 9H | 8H | 10H | 9H | 9H |

| kg/ha | C$_2$H$_5$-P(O)(OiPr)-CHCl-C(O)-O-iPr | 2-thienyl-P(O)(OC$_2$H$_5$)-CHCl-C(O)-O-iPr | | 4-F-Ph-P(O)(OC$_2$H$_5$)-CHCl-C(O)-O-iPr | | 2,6-(CH$_3$)$_2$-Ph-P(O)-CHCl-C(O)-O-iPr |
|---|---|---|---|---|---|---|
| | 2 | 0.4 | 0.4 | 2 | 0.4 | 0.4 |
| POST EMERGENCE | | | | | | |
| BUSH BEAN | 6H | 2H | 4G | 1B | 1H | 0 |
| COTTON | 3B,6H | 2B,2H | 1B,1H | 1B,3H | 1B,1H | 1B |
| MORNING GLORY | 1B | 1B | 1B | 1B | 1B,1H | 1B |
| COCKLEBUR | 1B | 0 | 0 | 1H | 3H | 1B |
| CASSIA | 1B,5H | 0 | 1H | 1B,5H | 1H | 1B,3H |
| NUTSEDGE | 6G | 0 | 5G | 1H | 0 | 0 |
| CRABGRASS | 9H | 6H | 9G | 9G | 7G | 7H |
| BARNYARD GRASS | 7H | 5H | 9H | 9H | 6H | 4H |
| WILD OATS | 0 | 0 | 2H | 0 | 0 | 0 |
| WHEAT | 6G | 0 | 2G | 5G | 0 | 0 |
| CORN | 8H | 3H | 0 | 7H | 0 | 0 |
| SOYBEAN | 6H | 3H | 1H | 1B,6H | 2H | — |
| RICE | 8G | 0 | 4G | 4G | 2G | 0 |
| SORGHUM | 8H | 0 | 2G | 1B,3G | 2G | 0 |
| PRE EMERGENCE | | | | | | |
| MORNING GLORY | 10H | 6H | 5H | 5H | 0 | 0 |
| COCKLEBUR | 8H | 0 | 0 | 0 | 0 | 0 |
| CASSIA | 9H | 6H | 6H | 7H | 5H | 2H |
| NUTSEDGE | 10E | 10E | 10E | 10E | 9G | 0 |
| CRABGRASS | 9H | 10H | 10H | 9H | 9H | 4G |
| BARNYARD GRASS | 9H | 9H | 10H | 10H | 10H | 9H |
| WILD OATS | 9H | 9H | 9H | 9H | 8H | 2G |
| WHEAT | 9H | 9H | 9H | 10E | 9H | 8G |
| CORN | 9H | 9H | 9H | 9H | 9H | 9H |
| SOYBEAN | 9H | 6H | 3H | 1H | 1H | 0 |

TABLE A-continued

| | | | | | | | |
|---|---|---|---|---|---|---|---|
| RICE | 10E | 10E | 10E | | 10E | 8H | 8G |
| SORGHUM | 9H | 9H | 9H | | 10H | 9H | 8H |

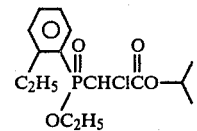

| | kg/ha | 2 | 0.4 |
|---|---|---|---|
| | POST EMERGENCE | | |
| | BUSH BEAN | 1B,6H | 1B,2H |
| | COTTON | 5B,7G | 1B,3H |
| | MORNING GLORY | 1B,7H | 1B |
| | COCKLEBUR | 1B | 0 |
| | CASSIA | 1B,5H | 0 |
| | NUTSEDGE | 7G | 3G |
| | CRABGRASS | 1C,8G | 1C,8G |
| | BARNYARD GRASS | 2C,9H | 9H |
| | WILD OATS | 1C,5H | 0 |
| | WHEAT | 7G,5X | 0 |
| | CORN | 9H | 5H |
| | SOYBEAN | 1B,3H | 2H |
| | RICE | 1B,6G | 3G |
| | SORGHUM | 2G | 0 |
| | PRE EMERGENCE | | |
| | MORNING GLORY | 9H | 0 |
| | COCKLEBUR | 1H | 0 |
| | CASSIA | 1C,5H | 0 |
| | NUTSEDGE | 10E | 10E |
| | CRABGRASS | 10E | 10E |
| | BARNYARD GRASS | 10H | 10H |
| | WILD OATS | 10E | 9H |
| | WHEAT | 10H | 9G |
| | CORN | 10H | 9H |
| | SOYBEAN | 7H | 0 |
| | RICE | 10E | 10E |
| | SORGHUM | 10H | 9H |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), morningglory (*Ipomoea hederacea*), cassia (Cassia tora), teaweed (*Sida spinosa*), velvetleaf (*Abutilon theophrasti*), and jimsonweed (*Datura stramonium*). A 12.5 cm diameter plastic pot as also filled with prepared soil and planted with rice and wheat. Another 12.5 cm pot was planted with sugarbeets. The above four containers were treated pre-emergence with a test compound from within the scope of the invention.

Twenty-eight days after treatment, the plants were evaluated and visually rated for response to the chemical treatments utilizing the rating system described previously for Test A. The data are summarized in Table B. Note that the compound is useful as a preemergence treatment for weed control in crops such as cotton and sugarbeets.

TABLE B

Pre-emergence

| Rate kg/ha | 0.06 | 0.12 | 0.50 |
|---|---|---|---|
| Crabgrass | 10H | 10H | 10E |
| Barnyardgrass | 8H | 10H | 10H |
| Sorghum | 0 | 9H | 10H |
| Wild oats | 3H | 0 | 10H |
| Johnsongrass | 6H | 9H | 10C |
| Dallisgrass | 8C | 10C | 10C |
| Giant foxtail | 10C | 10E | 10E |
| Ky. bluegrass | 9H | 10E | 10E |
| Cheatgrass | 3H | 9H | 10E |
| Corn | 0 | 1H | 10H |
| Mustard | 0 | 0 | 0 |
| Cocklebur | 0 | 0 | 0 |
| Nutsedge | 0 | 3G | 10E |
| Cotton | 0 | 0 | 3G |
| Morningglory | 0 | 0 | 3G |
| Cassia | 0 | 0 | 5G,3C |
| Teaweed | — | 0 | 0 |
| Velvetleaf | 0 | 0 | — |
| Jimsonweed | 0 | 5G | 7C |
| Soybean | 0 | 2G | 5H |
| Rice | 0 | 4G | 10C |
| Wheat | 0 | 4G | 7H |
| Sugarbeets | 0 | 0 | 0 |

Test C

Twenty-five cm diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberii*), and wild oats (*Avena fatua*). Approximately 2½ weeks after planting, the young plants and the soil around them were sprayed overall with the test chemical dissolved in a non-phytotoxic solvent. Fifteen days after treatment, all species were compared to untreated controls and visually rated for response to treatment. The rating system was as described previously for Test A. The data are presented in Table C. The compound tested by this procedure is useful for the post-emergence control of weeds.

TABLE C
Over-the-Top Soil/Foliage Treatment

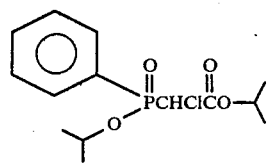

| Rate kg/ha | 0.12 | 0.50 |
| --- | --- | --- |
| Soybeans | 3H | 6H |
| Velvetleaf | 3H | 10C |
| Sesbania | 3H | 3H |
| Cassia | 4G | 5H |
| Cotton | 5H | 4H |
| Morningglory | 0 | 2C |
| Alfalfa | 2H | 6H |
| Jimsonweed | 3H | 5H |
| Cocklebur | 0 | 0 |

TABLE C-continued
Over-the-Top Soil/Foliage Treatment

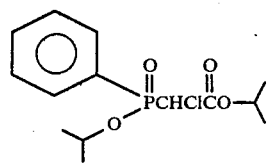

| Rate kg/ha | 0.12 | 0.50 |
| --- | --- | --- |
| Corn | 4H | 7H |
| Crabgrass | 3H | 7H |
| Rice | 0 | 6G, 2H |
| Nutsedge | 0 | 3H |
| Barnyardgrass | 7H | 7H |
| Wheat | 0 | 4G, 2H |
| Giant foxtail | 7H | 8H |
| Wild Oats | 2H | 8G, 4H |
| Sorghum | 0 | 7H |

I claim:

1. A compound of the formula

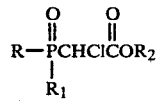

wherein

R is $C_1$–$C_4$ alkyl or phenyl;

$R_1$ is $C_1$–$C_4$ alkoxy; and $R_2$ is alkyl of 1 to 6 carbons, alkenyl of 3 to 4 carbons, cycloalkyl of 5–6 carbons or said cycloalkyl substituted with methyl.

2. The compound of claim 1, 1-methylethyl 2-chloro[(1-methylethoxy)phenylphosphinyl]acetate.

3. The compound of claim 1, 1-methylpropyl 2-chloro-2-[(1-methylethoxy)phenylphosphinyl]acetate.

4. The compound of claim 1, 1-methylethyl 2-chloro-2-[(n-butoxy)phenylphosphinyl]acetate.

5. The compound of claim 1, 1-methylethyl 2-chloro-2-[(1-methylethoxy)methylphosphinyl]acetate.

6. The compound of claim 1, 1-methylethyl 2-chloro-2-[(ethoxy)methylphosphinyl]acetate.

7. The compound of claim 1, 1-methylethyl 2-chloro-2-[(n-propoxy)phenylphosphinyl]acetate.

8. The compound of claim 1, 1-methylethyl 2-chloro-2-[(1-methylethoxy)ethylphosphinyl]acetate.

* * * * *